(12) United States Patent
Lorenzo

(10) Patent No.: US 12,419,646 B2
(45) Date of Patent: *Sep. 23, 2025

(54) MEDICAL DEVICE DELIVERY MEMBER WITH FLEXIBLE STRETCH RESISTANT MECHANICAL RELEASE

(71) Applicant: DePuy Synthes Products, Inc., Raynham, MA (US)

(72) Inventor: Juan Lorenzo, Davie, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 49 days.

This patent is subject to a terminal disclaimer.

(21) Appl. No.: 17/873,399

(22) Filed: Jul. 26, 2022

(65) Prior Publication Data

US 2022/0354502 A1  Nov. 10, 2022

Related U.S. Application Data

(63) Continuation of application No. 16/592,320, filed on Oct. 3, 2019, now Pat. No. 11,426,174.

(51) Int. Cl.
  *A61F 2/95* (2013.01)
  *A61B 17/00* (2006.01)
  *A61B 17/12* (2006.01)

(52) U.S. Cl.
  CPC .... *A61B 17/1214* (2013.01); *A61B 17/00234* (2013.01); *A61B 17/12113* (2013.01); *A61B 2017/00336* (2013.01)

(58) Field of Classification Search
  CPC .... A61F 2/07; A61F 2/95; A61F 2/966; A61F 2/958; A61F 2/954; A61B 17/00;
  (Continued)

(56) References Cited

U.S. PATENT DOCUMENTS 2,220,203 A  11/1940 Branin
3,429,408 A  2/1969 Maker et al.
(Continued)

FOREIGN PATENT DOCUMENTS

CN  102125451 A  7/2011
CN  103356260 A  10/2013
(Continued)

OTHER PUBLICATIONS

Translation of Japanese Office Action dated Apr. 16, 2024, in corresponding JP Appln. No. 2020-167536, and submitted herewith.
(Continued)

*Primary Examiner* — Vi X Nguyen
(74) *Attorney, Agent, or Firm* — TROUTMAN PEPPER LOCKE LLP

(57) ABSTRACT

A delivery system for delivering and deploying an implantable medical device is presented that includes a delivery member having a flexible distal portion. The deliver member can include a proximal hypotube, a flexible coil extending distally from the proximal hypotube, a compressible distal hypotube extending distally from the flexible coil, a sleeve extending along the flexible coil, and a loop wire. The loop wire can be effective to inhibit longitudinal elongation of the flexible coil. The sleeve can be effective to inhibit radial expansion of the flexible coil.

7 Claims, 5 Drawing Sheets

(58) Field of Classification Search
CPC .............. A61B 17/12; A61B 17/1214; A61B 17/00234; A61B 17/12113; A61B 2017/00336
See application file for complete search history.

(56) References Cited

U.S. PATENT DOCUMENTS

| | | |
|---|---|---|
| 4,858,810 A | 8/1989 | Intlekofer et al. |
| 5,108,407 A | 4/1992 | Geremia et al. |
| 5,122,136 A | 6/1992 | Guglielmi et al. |
| D329,698 S | 9/1992 | Loney et al. |
| 5,234,437 A | 8/1993 | Sepetka |
| 5,250,071 A * | 10/1993 | Palermo ............ G02B 26/0825 606/198 |
| 5,263,964 A | 11/1993 | Purdy |
| 5,334,210 A | 8/1994 | Gianturco |
| 5,350,397 A | 9/1994 | Palermo et al. |
| 5,382,259 A | 1/1995 | Phelps et al. |
| 5,392,791 A | 2/1995 | Nyman |
| 5,484,409 A | 1/1996 | Atkinson et al. |
| 5,536,248 A | 7/1996 | Weaver et al. |
| 5,569,221 A | 10/1996 | Houser et al. |
| 5,645,558 A * | 7/1997 | Horton ............ A61B 17/12172 606/198 |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,384,407 B2 | 6/2008 | Rodriguez et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 8,926,650 B2 | 1/2015 | Que et al. |
| 8,956,381 B2 | 2/2015 | Que et al. |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,718 B2 | 3/2018 | Lorenzo |
| 10,149,676 B2 | 12/2018 | Mirigian et al. |
| 10,285,710 B2 | 5/2019 | Lorenzo et al. |
| 10,292,851 B2 | 5/2019 | Gorochow |
| 10,420,563 B2 | 9/2019 | Hebert et al. |
| 10,517,604 B2 | 12/2019 | Bowman et al. |
| 10,668,258 B1 | 6/2020 | Calhoun et al. |
| 10,806,402 B2 | 10/2020 | Cadieu et al. |
| 10,806,461 B2 | 10/2020 | Lorenzo |
| 11,951,026 B2 | 4/2024 | Clinger et al. |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2002/0183786 A1 | 12/2002 | Girton |
| 2003/0009208 A1 | 1/2003 | Snyder et al. |
| 2003/0093094 A1 | 5/2003 | Diaz et al. |
| 2003/0181942 A1 | 9/2003 | Sutton et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2006/0025801 A1 | 2/2006 | Lulo et al. |
| 2006/0064151 A1 | 3/2006 | Guterman |
| 2006/0100687 A1 | 5/2006 | Fahey et al. |
| 2006/0116711 A1 | 6/2006 | Elliott et al. |
| 2006/0116714 A1 | 6/2006 | Sepetka et al. |
| 2006/0135986 A1 | 6/2006 | Wallace et al. |
| 2006/0206139 A1 | 9/2006 | Tekulve |
| 2006/0241685 A1 | 10/2006 | Wilson et al. |
| 2006/0247677 A1 | 11/2006 | Cheng et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0055302 A1 | 3/2007 | Henry et al. |
| 2007/0083132 A1 | 4/2007 | Sharrow |
| 2007/0203519 A1 | 8/2007 | Lorenzo et al. |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0045997 A1 | 2/2008 | Balgobin et al. |
| 2008/0097462 A1 | 4/2008 | Mitelberg et al. |
| 2008/0119887 A1 | 5/2008 | Que et al. |
| 2008/0269719 A1 | 10/2008 | Balgobin et al. |
| 2008/0269721 A1 | 10/2008 | Balgobin et al. |
| 2008/0281350 A1 | 11/2008 | Sepetka |

(56) References Cited

U.S. PATENT DOCUMENTS

| | | |
|---|---|---|
| 2008/0300616 A1 | 12/2008 | Que et al. |
| 2008/0306503 A1 | 12/2008 | Que et al. |
| 2009/0062726 A1 | 3/2009 | Ford et al. |
| 2009/0099592 A1 | 4/2009 | Buiser et al. |
| 2009/0270877 A1 | 10/2009 | Johnson et al. |
| 2009/0312748 A1 | 12/2009 | Johnson et al. |
| 2010/0094395 A1 | 4/2010 | Kellett |
| 2010/0114017 A1 | 5/2010 | Lenker et al. |
| 2010/0206453 A1 | 8/2010 | Leeflang et al. |
| 2010/0324649 A1 | 12/2010 | Mattsson |
| 2011/0092997 A1 | 4/2011 | Kang |
| 2011/0118772 A1 | 5/2011 | Chen et al. |
| 2011/0118776 A1 | 5/2011 | Chen et al. |
| 2011/0202085 A1 | 8/2011 | Loganathan et al. |
| 2011/0295303 A1 | 12/2011 | Freudenthal |
| 2012/0035707 A1 | 2/2012 | Mitelberg et al. |
| 2012/0041472 A1 | 2/2012 | Tan et al. |
| 2012/0083868 A1 | 4/2012 | Shrivastava et al. |
| 2012/0172913 A1 | 7/2012 | Kurrus et al. |
| 2012/0172921 A1 | 7/2012 | Yamanaka et al. |
| 2012/0179194 A1 | 7/2012 | Wilson et al. |
| 2012/0283768 A1 | 11/2012 | Cox et al. |
| 2012/0289772 A1 | 11/2012 | O'Connell et al. |
| 2013/0066413 A1 | 3/2013 | Jin et al. |
| 2013/0296915 A1 | 11/2013 | Bodewadt |
| 2013/0325054 A1 | 12/2013 | Watson |
| 2013/0338678 A1 | 12/2013 | Loushin et al. |
| 2014/0058435 A1 | 2/2014 | Jones et al. |
| 2014/0088565 A1 | 3/2014 | Vongphakdy et al. |
| 2014/0135812 A1 | 5/2014 | Divino et al. |
| 2014/0200607 A1 | 7/2014 | Sepetka et al. |
| 2014/0207175 A1 | 7/2014 | Aggerholm |
| 2014/0243883 A1 | 8/2014 | Tsukashima et al. |
| 2014/0277078 A1 | 9/2014 | Slazas et al. |
| 2014/0277084 A1 | 9/2014 | Mirigian et al. |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2014/0277100 A1 | 9/2014 | Kang |
| 2015/0005808 A1 | 1/2015 | Chouinard et al. |
| 2015/0025562 A1 | 1/2015 | Dinh et al. |
| 2015/0119884 A1 | 4/2015 | Fung et al. |
| 2015/0164666 A1 | 6/2015 | Johnson et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0022445 A1 | 1/2016 | Ruvalacaba et al. |
| 2016/0045347 A1 | 2/2016 | Smouse et al. |
| 2016/0157869 A1 | 6/2016 | Elgård et al. |
| 2016/0228125 A1 | 8/2016 | Pederson, Jr. et al. |
| 2016/0278782 A1 | 9/2016 | Anderson et al. |
| 2016/0310304 A1 | 10/2016 | Mialhe |
| 2016/0331383 A1 | 11/2016 | Hebert et al. |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072165 A1 | 3/2017 | Lim et al. |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105739 A1 | 4/2017 | Dias et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | von Oepen et al. |
| 2018/0036508 A1 | 2/2018 | Ozasa et al. |
| 2018/0078263 A1 | 3/2018 | Stoppenhagen et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0289375 A1 | 10/2018 | Hebert et al. |
| 2018/0296222 A1 | 10/2018 | Hebert et al. |
| 2018/0325706 A1 | 11/2018 | Hebert et al. |
| 2019/0142565 A1 | 5/2019 | Follmer et al. |
| 2019/0159784 A1 | 5/2019 | Sananes et al. |
| 2019/0192162 A1* | 6/2019 | Lorenzo ........... A61B 17/12022 |
| 2019/0201688 A1 | 7/2019 | Olson |
| 2019/0231566 A1 | 8/2019 | Tassoni et al. |
| 2019/0255290 A1 | 8/2019 | Snyder et al. |
| 2019/0314033 A1 | 10/2019 | Mirigian et al. |

(56) References Cited

U.S. PATENT DOCUMENTS

| | | |
|---|---|---|
| 2019/0328398 A1 | 10/2019 | Lorenzo |
| 2020/0015876 A1 | 1/2020 | Chou et al. |
| 2020/0078024 A1 | 3/2020 | Tekulve |
| 2020/0138448 A1 | 5/2020 | Dasnurkar et al. |
| 2020/0147347 A1 | 5/2020 | Cottone |
| 2020/0187951 A1 | 6/2020 | Blumenstyk |
| 2020/0229957 A1 | 7/2020 | Bardsley et al. |
| 2020/0397444 A1 | 12/2020 | Montidoro et al. |
| 2020/0406048 A1 | 12/2020 | Rentas Torres et al. |
| 2021/0001082 A1 | 1/2021 | Lorenzo et al. |
| 2021/0045759 A1 | 2/2021 | Merhi et al. |
| 2021/0085498 A1 | 3/2021 | N?ygaard et al. |
| 2021/0186513 A1 | 6/2021 | Hoshino et al. |
| 2021/0196281 A1 | 7/2021 | Blumenstyk et al. |
| 2021/0213252 A1 | 7/2021 | Lorenzo et al. |
| 2021/0338248 A1 | 11/2021 | Lorenzo et al. |
| 2021/0346002 A1 | 11/2021 | Lorenzo et al. |
| 2021/0353299 A1 | 11/2021 | Hamel et al. |

FOREIGN PATENT DOCUMENTS

| | | |
|---|---|---|
| CN | 104203341 A | 12/2014 |
| CN | 106456422 A | 2/2017 |
| CN | 109770985 A | 5/2019 |
| EP | 1985244 A2 | 10/2008 |
| EP | 2498691 | 9/2012 |
| EP | 3092956 A1 | 11/2016 |
| EP | 3501427 A1 | 6/2019 |
| EP | 3795097 A1 | 3/2021 |
| EP | 3799803 A1 | 4/2021 |
| EP | 3854321 A1 | 7/2021 |
| EP | 1188414 A1 | 3/2022 |
| EP | 4119065 A1 | 1/2023 |
| JP | H10-507090 A | 7/1998 |
| JP | 2006-334408 A | 12/2006 |
| JP | 2006346350 A | 12/2006 |
| JP | 2012-523943 A | 10/2012 |
| JP | 2013-78584 A | 5/2013 |
| JP | 2014-399 A | 1/2014 |
| JP | 2016-179174 A | 10/2016 |
| JP | 2017-529894 A | 10/2017 |
| WO | WO 2007/070793 A2 | 6/2007 |
| WO | WO 2008/064209 A1 | 5/2008 |
| WO | WO 2009/132045 A2 | 10/2009 |
| WO | WO 2012/158152 A1 | 11/2012 |
| WO | WO 2016/014985 A1 | 1/2016 |
| WO | WO 2017/066386 A1 | 4/2017 |
| WO | WO 2018/022186 A1 | 2/2018 |
| WO | WO 2020/148768 A1 | 7/2020 |

OTHER PUBLICATIONS

Examination Report dated May 8, 2023, in corresponding Application No. 20199892.9, and submitted herewith.

* cited by examiner

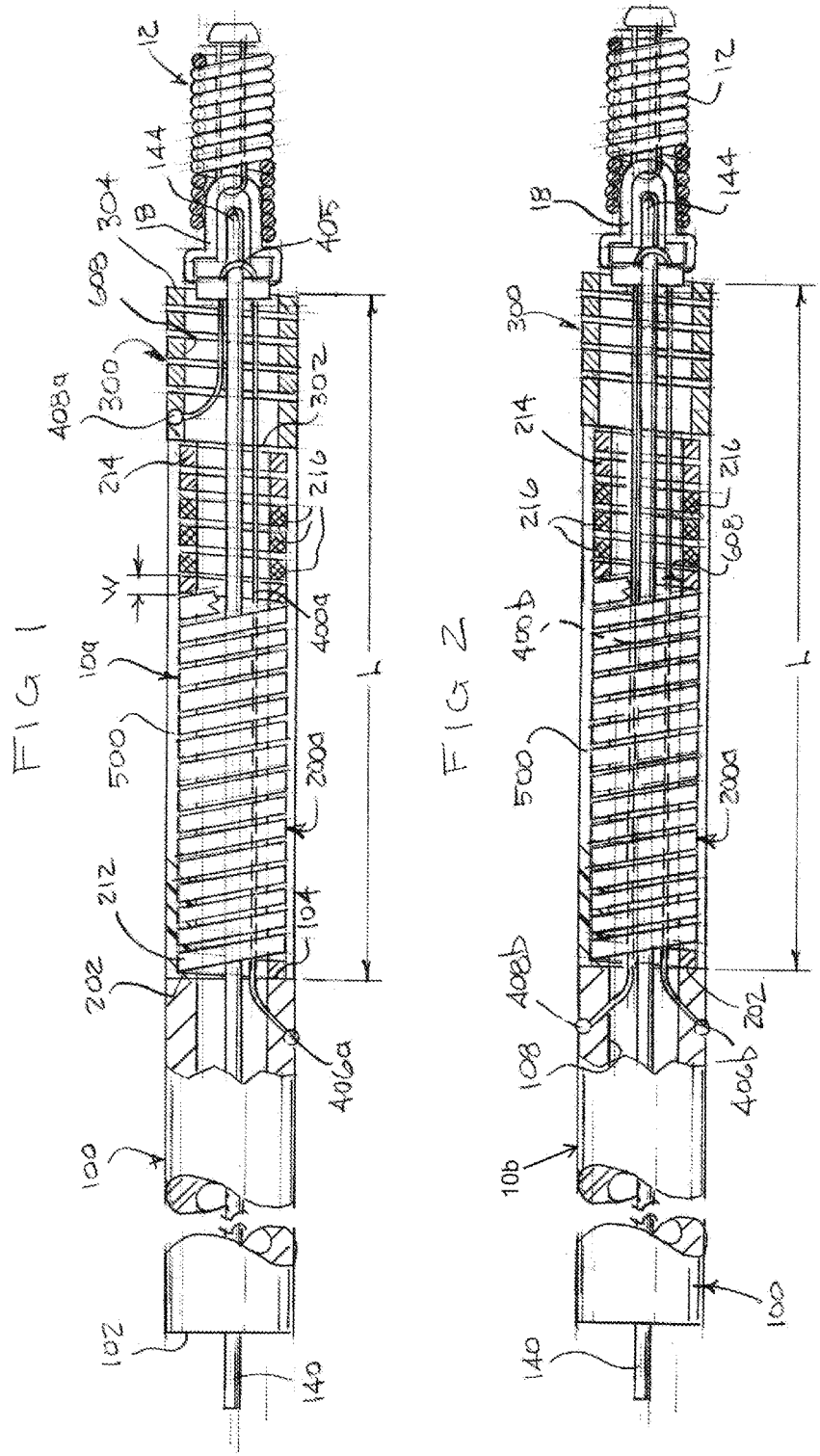

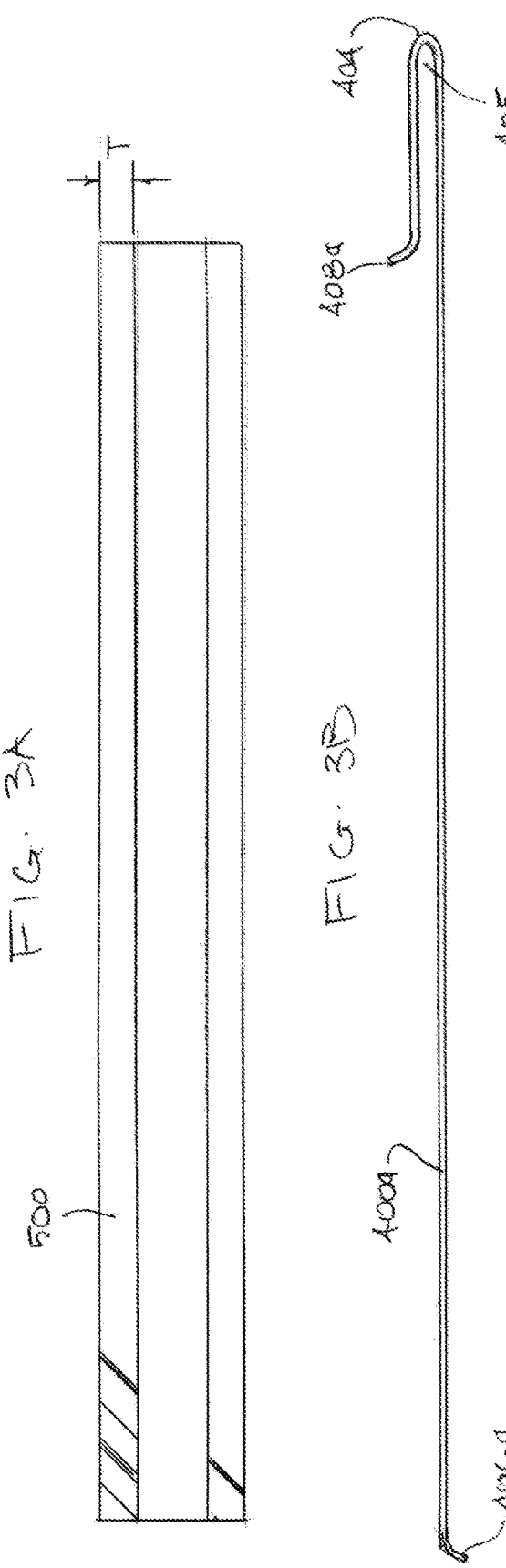
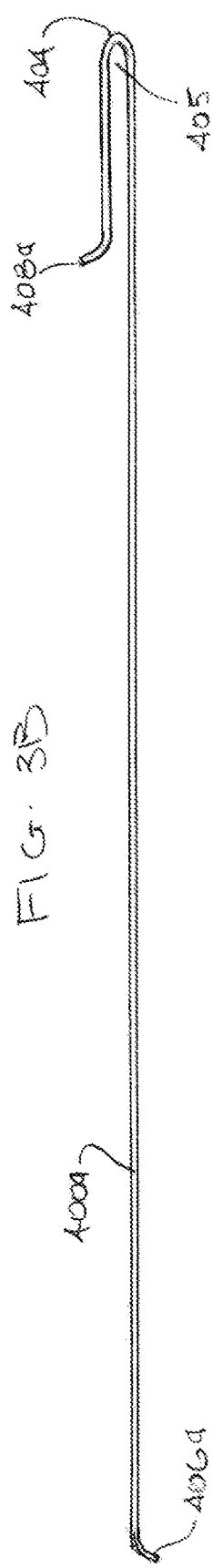
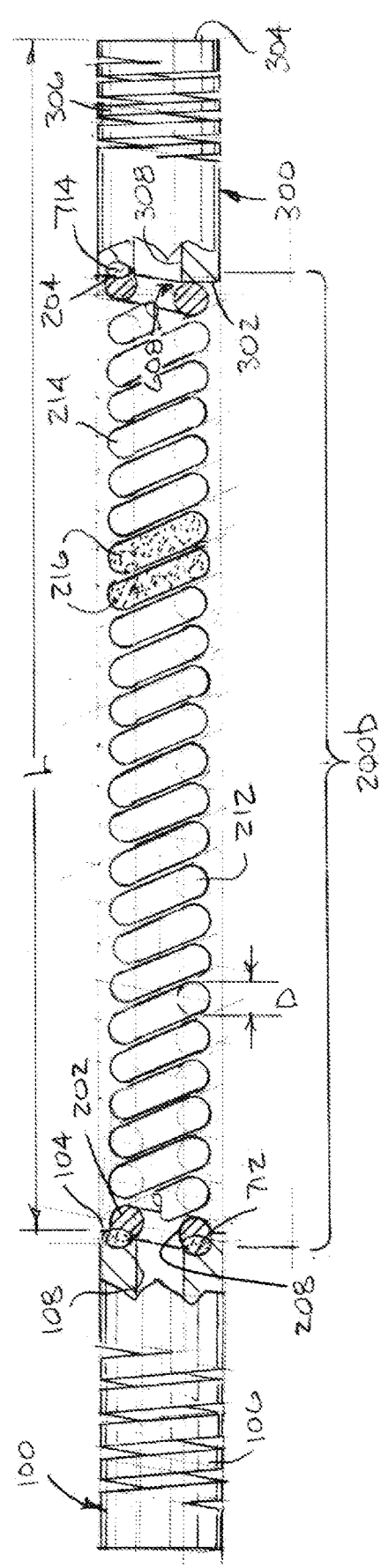
FIG. 3A
FIG. 3B
FIG. 3C

MEDICAL DEVICE DELIVERY MEMBER WITH FLEXIBLE STRETCH RESISTANT MECHANICAL RELEASE

CROSS REFERENCE TO RELATED APPLICATION

The present application is a continuation application of U.S. patent application Ser. No. 16/592,320 filed Oct. 3, 2019. The entire contents of which are hereby incorporated by reference.

FIELD OF INVENTION

This invention generally relates to intravascular medical device systems that navigable through body vessels of a human subject. More particularly, this invention relates to delivery systems and delivery members for delivering and deploying an implantable medical device to a target location of a body vessel and methods of using the same.

BACKGROUND

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, e.g. brain tissue, it can be difficult and often risky to perform surgical procedures to treat defects of the cranial blood vessels. Advancements in catheter-based implant delivery systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting a delivery catheter into the vasculature of a patient and guiding it through the vasculature to a predetermined delivery site. The delivery system can include an engagement/deployment system to releasably attach a vascular occlusion device, stent, or other intravascular treatment device to a delivery member (e.g. micro-catheter). The delivery member with the treatment device attached thereto can be pushed through the delivery catheter to the delivery site. Example delivery members and engagement/deployment systems are described in U.S. Patent Publication Number 2019/0192162 and U.S. patent application Ser. No. 15/964,857, (U.S. Publication No. 2019/0328398, U.S. Pat. No. 10,806,461), each incorporated herein by reference.

Some of the challenges that have been associated with properly executing such treatment procedures include ensuring the delivery member and engagement system remain in a stable position throughout a treatment. For example, in some aneurysm treatment applications, as the aneurysm becomes increasingly packed with embolic material, the delivery member can tend to shift due to increasing pushback from the embolic material being implanted. If the delivery member shifts during treatment, a physician may not be able to accurately control placement of embolic material and may choose to cease packing the aneurysm. In such an example, the aneurysm may not be sufficiently packed, which can lead to recanalization. Further, excessive movement or stretching of the delivery member and/or engagement system thereon can result in premature detachment of an embolic coil or other treatment device.

There is therefore a need for improved methods, devices, and systems to provide an implant delivery member and implant engagement system with increased stability.

SUMMARY

It is an object of the present invention to provide systems, devices, and methods to meet the above-stated needs. Generally, it is an object of the present invention to provide a delivery system for delivering and deploying an implantable medical device that includes a delivery member having a flexible distal portion.

Stiffness of the distal portion of the delivery member can cause the microcatheter used for delivery of the embolic material to pull back from the aneurysm as embolic material is pushed into a densely packed aneurysm. If the microcatheter pulls back while advancing the embolic material, the microcatheter may come out of the aneurysm or otherwise move out of position. In such circumstances, the physician may lose control of the embolic coil, may not be able to accurately control placement of embolic material, and/or may not be able to complete treatment.

Flexibility can be provided by incorporating a length of wound coil along the distal portion of the delivery member. The wound coil can be protected by a flexible polymer sleeve positioned around the outside of the coil. The wound coil can be inhibited from elongating by a stretch resistant loop wire positioned to extend through the wound coil and releasably secure the implant.

An example delivery system can be configured to deliver an implantable medical device to a target location of a body vessel. The example delivery system can include a proximal hypotube, a flexible coil extending distally from the proximal hypotube, a compressible distal hypotube extending distally from the flexible coil, a sleeve extending along the flexible coil, and a loop wire. The loop wire can be effective to inhibit longitudinal elongation of the flexible coil. The sleeve can be effective to inhibit radial expansion of the flexible coil.

The delivery system can further include a pull wire, that in conjunction with the loop wire, is effective to secure the implant to the delivery system. The loop wire and the pull wire can be movable to release the implant from the delivery system. The delivery system can include a lumen extending through the proximal hypotube, flexible coil, a distal hypotube. The loop wire and the pull wire can be positioned within the lumen. The loop wire can have a first end affixed to the proximal hypotube and a loop opening positioned to secure the implant to the delivery system. The loop opening can be positioned at the distal end of the compressible distal hypotube.

When the implant is secured to the delivery system, the loop opening can extend through an opening in the implant and the pull wire can extend through the loop opening. So configured, the loop wire can be under tension, inhibiting elongation of the flexible coil. The compressible distal portion can be compressed when the implant is secured to the delivery system such that the compressed distal portion provides tension to the loop wire and the loop wire inhibits elongation of the compressed distal portion.

The pull wire can be proximally retractable to exit the loop opening. The loop opening can be movable to exit the implant opening when the loop opening is unobstructed by the pull wire.

The sleeve can be effective to inhibit radial expansion of the flexible coil. The sleeve can cover most or all of the outer surface of the flexible coil.

The flexible coil can be more flexible than the proximal hypotube. The flexible coil can also be more flexible than the compressible distal hypotube. The flexible coil can include one or more non-radiopaque sections and one or more radiopaque sections. The flexible coil can include two non-radiopaque sections separated by a radiopaque section such that the non-radiopaque sections extend from a proximal and distal end of the flexible coil and the radiopaque section is between the non-radiopaque sections. The flexible coil can be constructed from a wound wire. The wound wire can define a portion of the lumen of the delivery system. The wire strand that is wound can have a strand diameter measuring from about 0.8 thousandths of an inch to about 5 thousandths of an inch, or about 20 micrometers to about 130 micrometers. The strand of the wire can have a substantially circular cross section.

The length of a distal portion of the delivery system can be measured from the distal end of the compressible distal hypotube to the proximal end of the flexible coil. The length of the distal portion can measure from about 30 cm to about 50 cm, or more specifically about 40 cm.

The compressible distal hypotube can include a spiral cut. The compressible distal hypotube can be compressed due to tension in the loop wire when the implant is secured to the delivery system. The compressible distal hypotube can be movable to decompress upon movement of the loop wire and the pull wire to release the implant.

An example method can include step for designing or constructing a delivery member such as the example above. The method can include connecting a distal end of a proximal tube to a proximal end of the coiled wire, connecting a distal end of the coiled wire to a proximal end of a compressible distal tube, positioning a sleeve along a majority of the length of the coiled wire, inhibiting radial expansion of the coiled wire with the sleeve, affixing a loop wire to the proximal tube, positioning a loop opening in the loop wire at a distal end of the distal tube while the loop wire is affixed to the proximal tube such that the loop wire is extended through the coiled wire, and inhibiting longitudinal elongation of the coiled wire with the loop wire. The proximal tube, coiled wire, and compressible tube can be connected to form a lumen that extends through the three parts.

The distal tube can be compressed and, while the loop wire is affixed to the proximal tube and the distal tube is compressed, the loop opening can be positioned at the distal end of the distal tube and the loop wire can be used to secure the implant to the delivery tube. Once the implant is secured, tension in the loop wire can maintain compression of the distal tube and inhibit longitudinal expansion of the coiled wire. The sleeve can inhibit radial expansion of the tube.

An intravascular implant can be secured to the delivery tube by extending a pull wire through the lumen of the three parts, extending the loop opening through a locking portion of the intravascular implant, and extending a distal end of the pull wire through the loop opening. The implant can be secured such that during treatment, the implant can be released from the distal tube by retracting the distal end of the pull wire from the loop opening and retracting the loop opening from the locking portion of the intravascular implant.

The coiled wire and the sleeve can be selected such that when the sleeve is in position along most of the length of the coiled wire, the combination of the sleeve and coiled wire is more flexible than both the proximal hypotube and the compressible distal tube.

The coiled wire can be selected such that the coiled wire includes a wire wound to define a portion of the lumen extending through the coiled wire. The wire which is wound to form the lumen can itself have a cross-sectional diameter measuring from about 0.8 thousandths of an inch to about 5 thousandths of an inch, or about 20 micrometers to about 130 micrometers.

A radiopaque coiled section can be positioned in the coiled wire.

The coiled wire and the compressible distal tube can be sized to have a length measurable from the distal end of the distal tube to the proximal end of the coiled wire such that the length measures from about 30 cm to about 50 cm, or more specifically about 40 cm.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 is an illustration of a delivery system and implant according to aspects of the present invention;

FIG. 2 is an illustration of another delivery system and implant according to aspects of the present invention;

FIGS. 3A through 3C are illustrations of component parts of a delivery system according to aspects of the present invention;

DETAILED DESCRIPTION

Figure 4A:
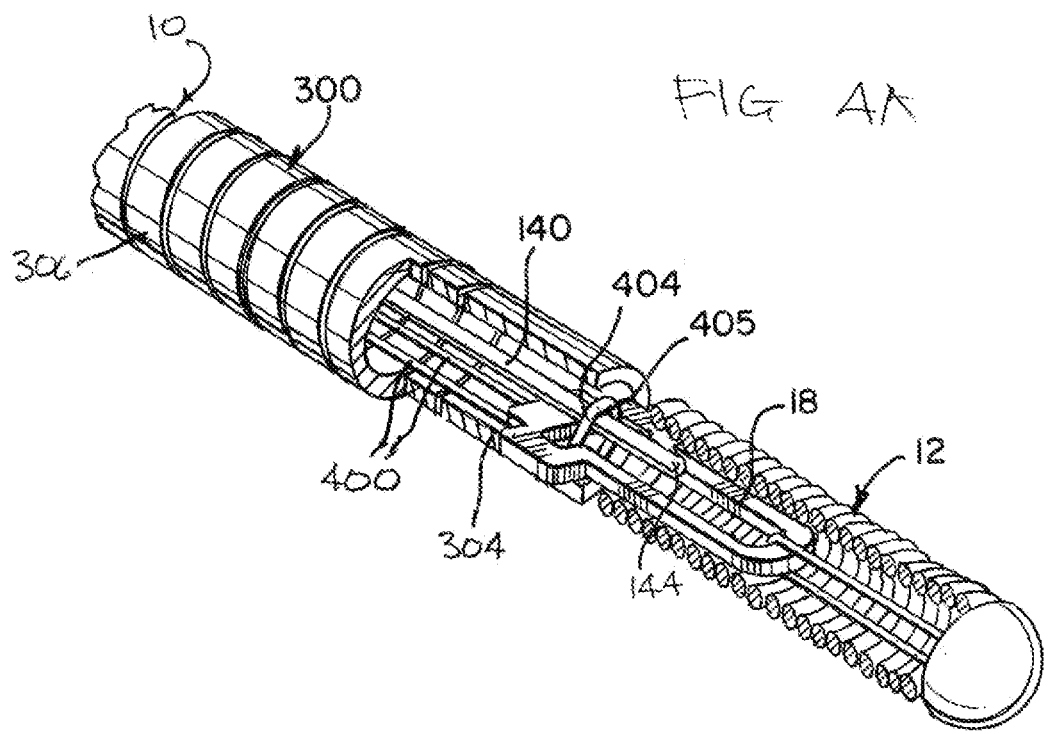
FIGS. 4A through 4D illustrate the release of an implant from a delivery system according to aspects of the present invention.

A key success factor in intravascular treatment such as aneurysm treatments is for the delivery member (e.g. microcatheter) to remain stable during the deployment of an implant or other medical treatment device. During an intravascular treatment, lack of flexibility of a distal portion of a treatment device delivery member can cause the delivery member to pull back from the treatment site or otherwise move out of position while the implant is being placed in an aneurysm or other treatment site. A delivery member and engagement system having a more flexible distal portion can therefore provide a stable system for delivering medical devices in neurovascular anatomy in addition to other applications facing a similar challenge. Flexible structures, however, can tend to deform, extend, or expand when navigating tortuous anatomy. Deformation of the delivery member can inhibit the delivery member's ability to navigate to a treatment site and/or effectively deploy the medical device. Elongation of the delivery member can result in premature deployment of the medical device.

An object of the present invention is to provide a delivery member having a highly flexible distal portion that is stretch resistant and structurally stable throughout delivery and deployment of a medical treatment device. For ease of discussion, medical treatment devices are generally referred to herein as an "implant" although, as will be appreciated and understood by a person of ordinary skill in the art, aspects of the present invention can be applied to deliver and deploy medical treatment devices that are not left implanted.

According to the present invention, in some examples, a delivery member can include a proximal elongated delivery hypotube, a coiled assembly attached to the distal end of the proximal hypotube, and a laser cut spiraled segment attached distally to the coiled assembly. The coiled assembly can be designed to be highly flexible. The coiled assembly can include a coiled wire covered by an outer sleeve. The coiled wire can include one or more radiopaque coiled segments concentrically welded near a distal section of the coiled assembly.

The proximal hypotube can extend a majority of the length of the delivery member such that the coiled assembly and the distal laser cut spiraled hypotube extend over about 30 cm to about 50 cm, or more specifically about 40 cm, from the distal end of the delivery member. The distal spiraled hypotube can be axially compressed in a similar manner to a spring.

The assembly of tubes and coiled assembly can contain within its lumen a pull wire and a locking member in the form of a loop wire that together are positioned to secure an implant to the delivery member. The implant can be detached by displacing the pull wire proximally until the pull wire clears the locking member allowing the implant to be released from the delivery member.

The loop wire can be constructed of a stretch resistant fiber having two ends. One leg of the loop wire can be connected at the proximal end of the laser cut spiraled distal hypotube while the other leg can be connected in the proximal direction in relation to the proximal end of the coiled assembly. The leg stretching proximal to the coiled assembly and extending to the proximal end of the spiral cut hypotube can serve the function of a stretch resistant member to prevent the very flexible coiled assembly from stretching as the delivery member is manipulated during delivery of the implant which could result in premature detachment of the implant. Alternatively, both legs of the loop wire can be attached proximal to the proximal end of the coiled assembly. In some applications, two legs extended through the coiled assembly can provide improved stretch resistant of the coiled assembly compared to a single leg extending through the coiled assembly.

In some applications, for instance if the implant is an embolic coil, it can be desirable to minimize insertion of the pull wire into the implant in order to minimize stiffening of the proximal end of the implant. However, it can also be desirable to extend the pull wire through the loop wire with sufficient length to minimize the likelihood that the pull wire disengages from the loop wire due to the pull wire shifting and/or the delivery member deforming, thereby prematurely releasing the implant. In some applications, the stretch resistance of the loop wire can inhibit elongation of the delivery member, thereby reducing the likelihood of prematurely releasing the implant and/or allowing the pull wire to be positioned with a shorter length into the implant thereby increasing flexibility at the proximal end of the implant.

Turning to the figures, as illustrated in FIGS. 1, 2, and 3A through 3C an example delivery member 10a, 10b can include a proximal tube 100, a coiled section 200a, 200b, a distal tube 300, a sleeve 500 surrounding the coiled section, and a loop wire 400a, 400b extending through the coiled section 200a, 200b. The delivery member 10a, 10b can have a lumen 608 therethrough extending through the proximal tube 100, coiled section 200a, 200b, distal tube 300. In other words, the proximal tube 100 can have a lumen 108 therethrough, the coiled section 200a, 200b can have a lumen 208 therethrough, the distal tube 300 can have a lumen 308 therethrough, and the lumens 108, 208, 308 can be contiguous to form the lumen 608 through the delivery member 10a, 10b. The proximal tube 100 can have a distal end 104 connected to a proximal end 202 of the coiled section 200a, 200b, and a distal end 204 of the coiled section 200a, 200b can be connected to a proximal end 302 of the distal tube 300.

When the delivery member 10a, 10b is assembled, the coiled section 200a, 200b and sleeve 500 can be more flexible than the distal hypotube and the proximal hypotube. One way to measure flexibility is to perform a three-point bend test wherein a portion of the delivery member 10a, 10b is held fixed at two end points, a force is applied perpendicularly to the member 10a, 10b centrally between the points, and flexibility is quantified by the length of deflection of the delivery member 10a, 10b caused by the force. When measured this way, in some examples, the coiled section 200a, 200b and sleeve 500 can be about 1.5 times more flexible than the distal hypotube and about 20 times more flexible than the proximal hypotube 100. In other words, when the three-point test is performed identically on the three sections 100, 200a, 200a, 300, the coiled section can deflect over a length that is about 1.5 time the deflection length of the distal hypotube and about 20 times the length of deflection of the proximal hypotube. Flexibility can be measured in other ways as would be appreciated and understood by a person of ordinary skill in the art. When the delivery member 10a, 10b is assembled, the coiled section 200a, 200b and sleeve 500 can be more flexible than the distal hypotube and the proximal hypotube as flexibility is determined by other means as would be known to a person of ordinary skill in the art.

Delivery members 10a, 10b manufactured according to the illustrations in FIG. 1 and FIG. 2 are demonstrated to have a flexibility of about 25% to about 40% greater than competing delivery systems.

Comparing the delivery member 10a illustrated in FIG. 1 to the delivery member 10b illustrated in FIG. 2, in FIG. 1, the loop wire 400a is illustrated as having a first end attachment 406a to the proximal tube 100 and a second end attachment 408a to the distal tube 300 while, in FIG. 2, the loop wire 400b is illustrated as having a first and second end attachment 406b, 408b both to the proximal tube 100. Although several factors can contribute to the flexibility of the delivery member, all else being equal, the delivery member 10a illustrated in FIG. 1 can be more flexible compared to the delivery member 10b illustrated in FIG. 2 because the delivery member 10a illustrated in FIG. 1 has a single leg of loop wire 400a passing through the coiled section 200a and therefore less material passing through the coiled section 200a compared to the delivery member 10b of FIG. 2 which has two legs of the loop wire 400b passing through the coiled section 200b. Alternative configurations are also contemplated, for instance the loop wire need not have two separable ends, e.g. the legs of the loop wire can be fused, twisted, or otherwise formed as a single unit.

FIGS. 3A through 3C illustrate component parts of an example delivery system with the sleeve 500 illustrated in FIG. 3A, the loop wire 400a illustrated in FIG. 3B, and an assembly including the proximal tube 100, coiled section 200b, and distal tube 300 in FIG. 3C. Comparing the example delivery member 10a illustrated in FIG. 1 to the component parts illustrated in FIGS. 3A through 3C, in FIG. 1, the winding of the coiled section 200a has a substantially square shaped cross section while, in FIG. 3C, the winding of the coiled section 200b has a substantially circular cross section. The coiled wire can be formed of a substantially linear wire that is wound in a coil shape and/or a hypotube that is laser cut in a spiral pattern. If the coiled wire is formed from a laser cut hypotube, the spiral can be absent interference cuts connecting windings in the coil so as to provide a more flexible coil. A coiled section formed from a laser cut hypotube can have a substantially square shaped cross section as illustrated by the coiled section 200a in FIG. 1 and FIG. 2. A coiled section formed from a linear wire wound into a coil shape can have a substantially circular cross section as illustrated by the coiled section 200b in FIG. 3C.

Comparing the exemplary delivery member 10a illustrated in FIG. 1 to the component parts illustrated in FIGS. 3A through 3C, in FIG. 3C, the proximal hypotube 100 can include a flexible section 106 having material removed to increase flexibility of the flexible section 106. The flexible section 106 can be cut in a spiral pattern. The spiral pattern of the flexible section 106 can lack interference cuts connecting windings within the spiral. The proximal attachment end 406a of the loop wire 400 can be attached to the proximal tube 100 in the proximal direction relative to the flexible section 106 of the proximal tube 100. The loop wire 400a can thereby inhibit elongation of the flexible section 106 of the proximal tube 100 and coiled section 200b. The sleeve 500 can cover at least a portion of the flexible section 106 to inhibit deformation of the flexible section and/or reduce friction with vasculature and the flexible section 106 during intravascular navigation. In some examples, the sleeve 500 can cover about 10 cm of the proximal tube 100 approximate and/or including the distal end 104 of the proximal tube 100.

Referring collectively to FIGS. 1 through 3C, the coiled section 200a, 200b can be formed separately from the proximal hypotube 100 and/or the distal hypotube 300. The separately formed coiled section 200a, 200b can be affixed with welds 712, 714 or other appropriate attachment to the proximal tube 100 and/or the distal tube 300. Alternatively, or additionally, at least a portion of the coiled section can be formed from a spiral laser cut portion of a hypotube. A separately formed coiled section 200b can be made more flexible compared to a spiral cut tube 200a by selecting a wire with a particular cross section (e.g. circular) with a particular diameter D, or by selecting a wire with material properties to increase flexibility. Conversely, a laser cut portion 200a can be more easily fabricated by cutting a single hypotube to form the proximal tube 100, coiled section 200a, and distal hypotube 300, reducing or eliminating welds 712, 714 or other attachments. In either case, the wire of the coil 200a, 200b can have a diameter D or width W measuring within a range including about 0.8 mils and 5 mils (about 20 nm to about 130 nm).

The coiled section can be formed primarily of a non-radiopaque material such as steel and can include a radiopaque section 216 made of a radiopaque material such as platinum and/or tungsten. The radiopaque section 216 can be positioned between a proximal, non-radiopaque section of the coil 212 and a distal, non-radiopaque section of the coil 214. The radiopaque section 216 can be positioned a predetermined distance from a distal end 304 of the delivery member 10a, 10b so that a physician can readily visualize the placement of the distal portion of the delivery member during a treatment procedure. The proximal section 212, radiopaque section 216, and distal section 214 can be concentrically welded.

The coiled section 200a, 200b can be surrounded by a flexible sleeve or fused jacket 500, referred generically herein as a "sleeve". The sleeve can inhibit the coil 200a, 200b from expanding radially and/or from engaging vascular walls during navigation. The sleeve 500 can include a polymer. The polymer can include additives to increase the lubricity of the sleeve 500 so that the sleeve can easily slide through a body vessel. As illustrated in FIG. 2A, the sleeve 500 can have a wall thickness T measuring within a range including about 0.5 mils and about 2 mils (about 0.01 mm to about 0.05 mm). The sleeve 500 can further be coated with a hydrophilic coating to further minimize friction during intravascular navigation. The sleeve 500 can be fused or glued to the coil 200a, 200b, the proximal hypotube 100, and/or the distal hypotube 300.

The proximal tube 100 can extend a majority of the length of the delivery member 10a, 10b with the coiled section 200a, 200b and distal tube 300 forming a length L sufficient to absorb a majority of push-back that can occur during placement of an implant at a treatment site. When the proximal tube includes a flexible section 106, the length L can include the distal tube 300, coiled section 200a, 200b, and the flexible section 106 of the proximal tube, measured from the proximal end of the flexible section 106 to the distal end of the distal tube 300. In some examples, the length L can measure between about 30 cm and about 50 cm, or more specifically, about 40 cm.

In some examples, it can be advantageous to have a relatively stiff proximal hypotube 100, a relatively flexible distal compressible tube 300, and a flexible coil 200a, 200b and sleeve 500 assembly that is more flexible than both the proximal hypotube 100 and the distal compressible tube 300. The proximal hypotube 100 can be sufficiently stiff over a majority of its length to resist kinking while being pushed through the microcatheter. The flexible coil 200a, 200b and distal compressible tube 300 can each be sufficiently flexible to reduce the effects of push-back when an implant 12 is being placed in an aneurysm. Because the flexible coil 200a, 200b need not be compressibly resilient, the flexible coil can have greater flexibility than the distal compressible tube.

In some examples, the flexible coil 200a, 200b and sleeve 500 assembly can be about 25% more flexible than the distal compressible tube 300. In some examples, the flexible coil 200a, 200b and sleeve 500 assembly can be about 20 times more flexible than the proximal hypotube 100. Flexibility can be measured using a three-point bend test or other appropriate test as would be appreciated and understood by a person of ordinary skill in the art. Generally, a three-point bend test can be performed by fixing a tube portion at two points and applying a force in between the two points. Flexibility can be quantified by a length of displacement of the tube portion for a predetermined force and/or by a magnitude of force to displace the tube by a predetermined length.

FIGS. 1, 2, and 4A each illustrate an implant 12 secured to a delivery member 10a, 10b, 10 by a mechanical engagement system including the loop wire 400a, 400b, 400 and an inner elongated member 140 that can be manipulated at the proximal end by a physician to deploy the implant 12. Such a wire or inner elongated member is referred to herein generically as a "pull wire" 140. Referring collectively to FIGS. 1, 2, and 4A, the combination of the coil 200a, 200b, sleeve 500, and loop wire 400, 400a, 400b can provide a highly flexible distal portion of a delivery member 10, 10a, 10b suitable for navigating tortuous anatomy, including neurovascular blood vessels. The loop wire 400, 400a, 400b can support the coil 200a, 200b to prevent the coil 200a, 200b from significantly elongating during navigation of a blood vessel, thereby reducing tension on the pull wire's 140 engagement to the loop opening 405 and reducing the likelihood of premature deployment of an attached medical treatment device 12.

Referring collectively to FIGS. 1, 2, 3C, and 4A through 4C, the distal tube 300 can include a compressible portion 306. The compressible portion 306 can be axially adjustable between an elongated condition and a compressed condition. The compressed portion 306 can be formed from a spiral-cut portion of the tube 300, formed by a laser cutting operation. Additionally, or alternatively, the compressible portion can be formed of a wound wire, spiral ribbon, or other arrangement allowing axial adjustment according to the present invention. Preferably, the compressible portion 306 is in the elongated condition at rest and automatically or resiliently returns to the elongated condition from a compressed condition, unless otherwise constrained.

Figure 4B:
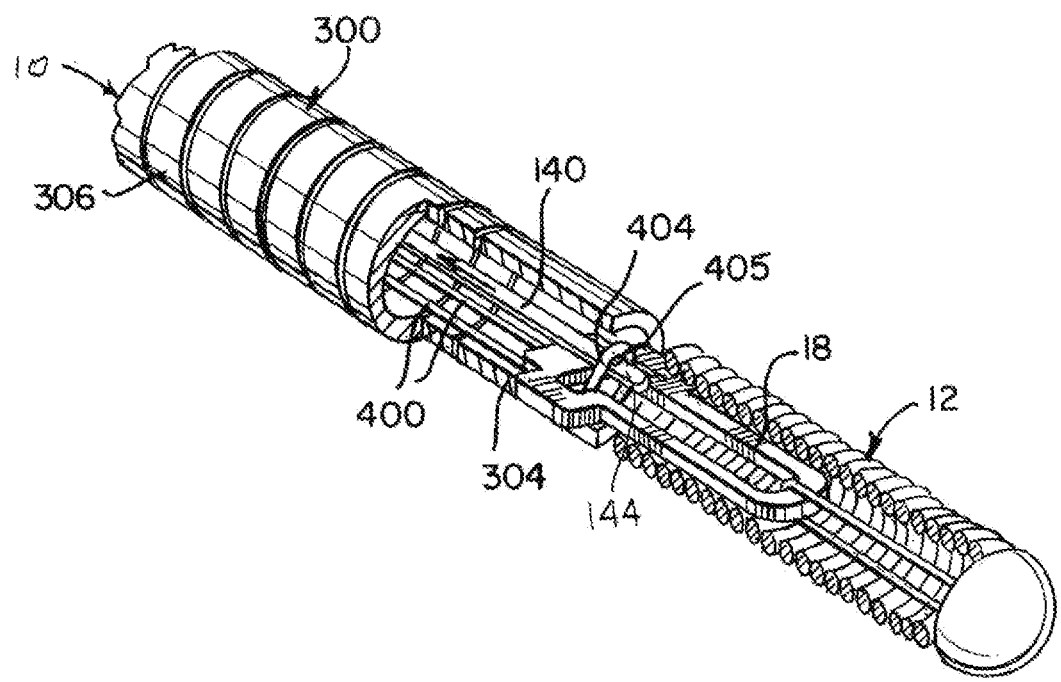
Figure 4C:
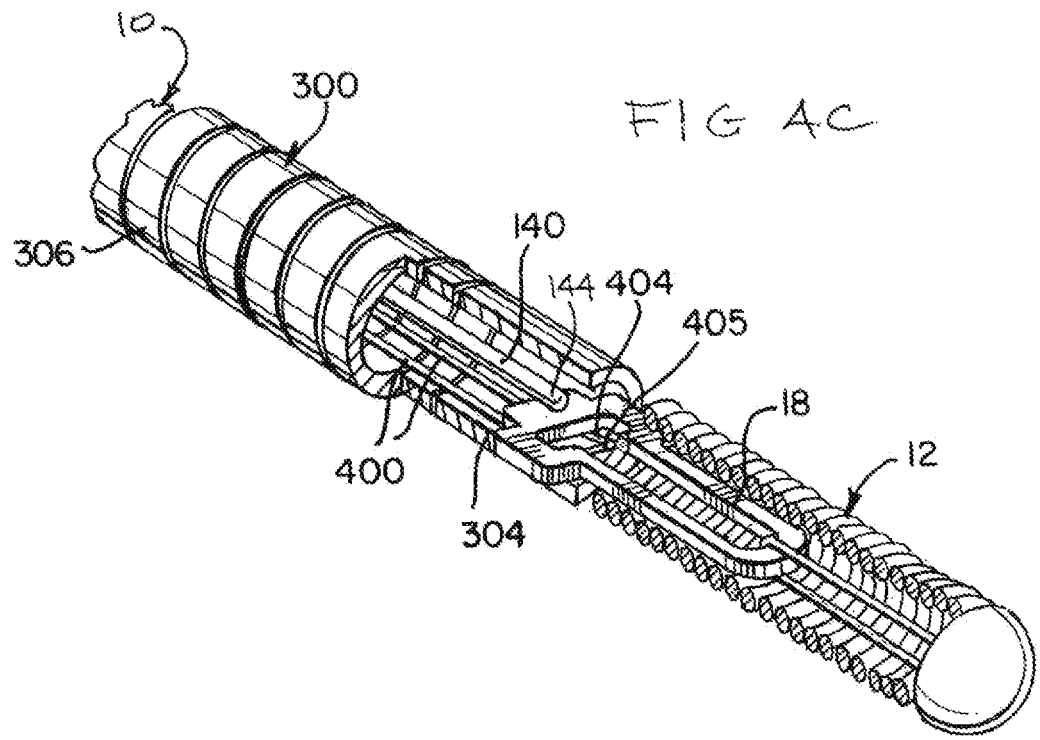
Figure 4D:
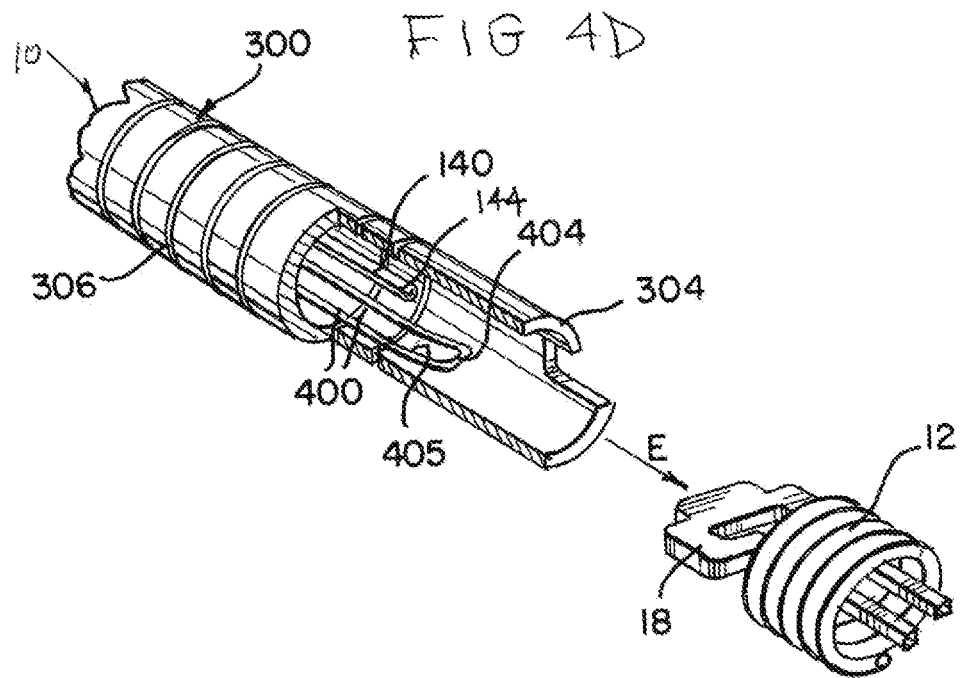

FIGS. 4A through 4D are a time sequence set of illustrations depicting release of a medical device (e.g. implant) 12 from a delivery member 10. The delivery member 10 can be configured such as illustrated in FIGS. 1 through 3C and otherwise described herein. FIG. 4A illustrates an engagement system including the loop wire 400 and pull wire 140 locked into a locking portion 18 of the medical device 12. The compressible portion 306 of the distal tube 300 can be compressed and the loop wire 400 opening 405 at a distal end 404 of the loop wire 400 can be placed through the locking portion 18. When the pull wire 140 is put through the opening 405 the medical device 12 is now secure. FIG. 4B illustrates the pull wire 140 being drawn proximally to begin the release sequence for the medical device 12. FIG. 4C illustrates the instant the distal end 144 of the pull wire 140 exits the opening 405 and the pull wire 140 is pulled free of the loop wire 400. The distal end 404 of the loop wire 400 falls away and exits the locking portion 18. As can be seen, there is now nothing holding the medical device 12 to the detachment system 10. FIG. 4D illustrates the end of the release sequence. Here, the compressible portion 306 has extended/returned to its original shape and "sprung" forward. An elastic force E is imparted by the distal end 304 of the distal tube 300 to the medical device 12 to "push" it away to ensure a clean separation and delivery of the medical device 12.

The compressible portion 306 can have a difference in length (distance of compression) when measured in the compressed configuration and the original, uncompressed configuration of about 0.5 mm to about 0.75 mm. Greater elastic force E can be achieved by using a greater distance of compression. The distance of compression can be determined by the sizing of the loop wire 400, the shape of the locking portion 18, and the shape of the distal end 304 of the distal tube 300.

Figure 5:
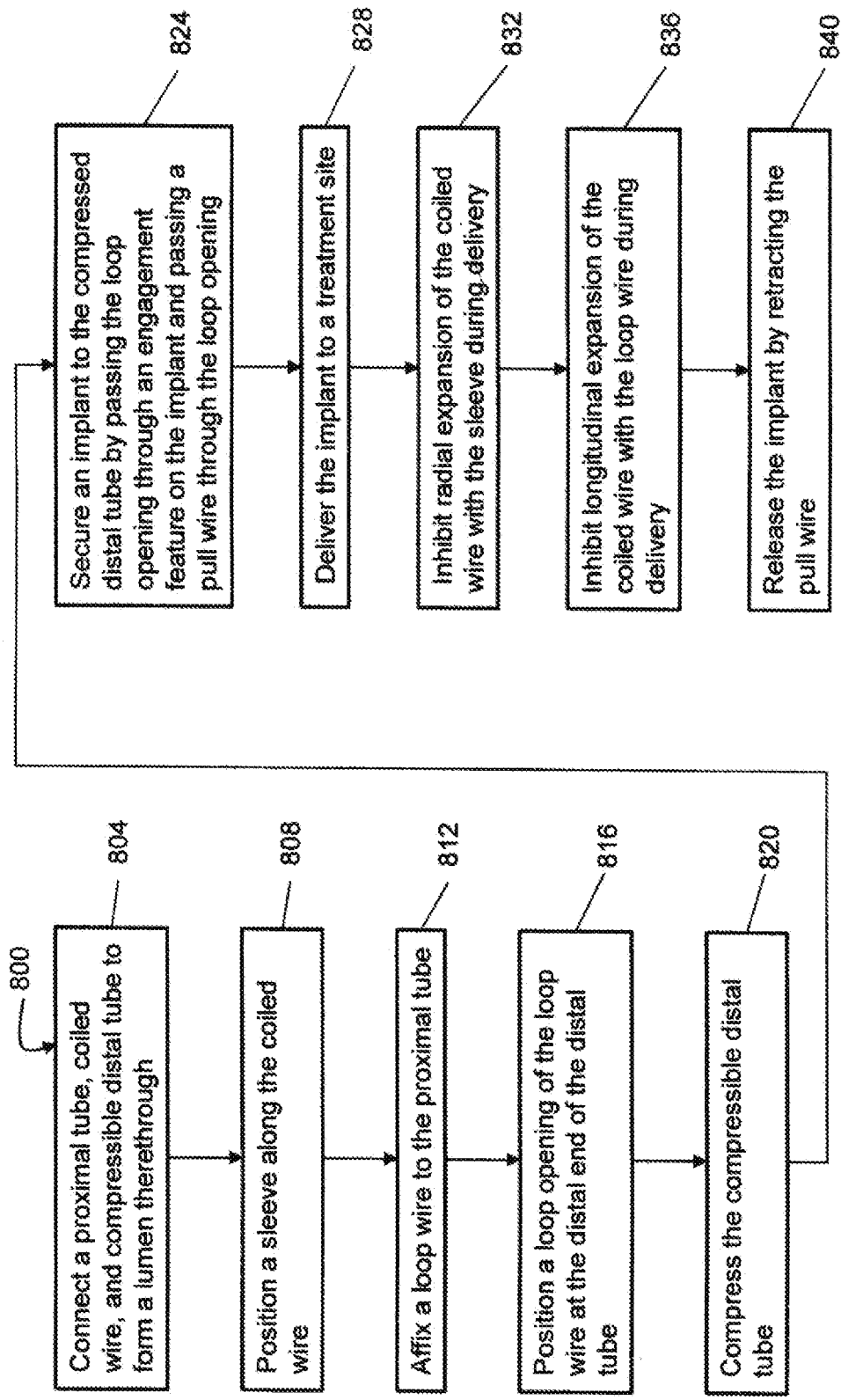
FIG. 5 is a flow diagram illustrating steps for designing, constructing, or configuring a delivery system and implant and delivering the implant according to aspects of the present invention.

FIG. 5 is a flow diagram outlining example method steps of a method 800 for treating an aneurysm. Steps 804, 808, 812, 816, 820, and 824 are generally directed toward designing, constructing, or configuring a delivery system such as an example system presented herein, a variation thereof, and alternative implant delivery systems as would be appreciated and understood by a person of ordinary skill in the art. Steps 828, 832, 836, and 840 are directed toward delivering and deploying an implant with the delivery system designed, constructed, or configured according to one or more of the preceding method steps.

In step 804, a proximal tube, coiled wire, and a compressible distal tube can be connected such that the assembly is substantially tubular and has a contiguous lumen extending through the assembled sections. The proximal tube, the coiled wire, and the compressible distal tube can each respectively be a proximal tube 100, support coil 200a, 200b, and distal hypotube 300 such as described and/or illustrated herein, a variation thereof, or an alternative as would be appreciated and understood by a person of ordinary skill in the art.

In step 808, a sleeve can be positioned along the coiled wire. The sleeve can be a sleeve 500 such as described and/or illustrated herein, a variation thereof, or an alternative as would be appreciated and understood by a person of ordinary skill in the art. The sleeve can be positioned to surround a portion of the length of the coiled wire, or the entire length of the coiled wire. The sleeve can also be positioned to extend to cover a respective portion of one or both of the proximal tube and the distal tube.

In step 812, a loop wire can be affixed to the proximal tube. The loop wire can be a loop wire 400, 400a, 400b such as described and/or illustrated herein, a variation thereof, or an alternative as would be appreciated and understood by a person of ordinary skill in the art. The loop wire can have two ends, at least one of the two ends can be affixed to the proximal tube in step 812, and a loop opening can be defined as a bend in the loop wire between the two ends. An end not affixed to the proximal tube in step 812 can be affixed to the delivery member at the distal tube or other location. Alternatively, the loop wire can have a single end that is affixed to the proximal tube in step 812 and a loop opening formed at an opposite end of the loop wire.

In step 816, the loop opening of the loop wire can be positioned at a distal end of the distal tube. The loop opening can be positioned as described and/or illustrated herein or otherwise positioned to facilitate attachment of an implant at the distal end of the distal tube.

In step 820, the compressible distal tube can be compressed.

In step 824, an implant can be secured to the compressed distal tube by passing the loop opening through an engagement feature (locking portion or opening) on the implant and passing a pull wire through the loop opening.

In step 828, the implant can be delivered to a treatment site. The implant can be an implant 10, 10a, 10b as described and/or illustrated herein, a variation thereof, or an alternative medical treatment device as would be appreciated and understood by a person of ordinary skill in the art. The implant can be delivered by means known to a person of ordinary skill in the art. In some examples, the treatment site can be an intravascular treatment site such as an aneurysm or lesion. The implant can be delivered through a catheter positioned intravascularly. A portion of a delivery system (e.g. the proximal tube) can be accessible by a physician such that the physician can push the delivery system into the patient and through the catheter. The implant can be attached at the distal end of the delivery system and pushed by the delivery system as the delivery system is pushed by the physician further into the catheter.

In step 832, the sleeve can inhibit radial expansion of the coil as the implant is being delivered to the treatment site. The sleeve can inhibit radial expansion of the coil by means described herein, variations thereof, or alternatives as would be appreciated and understood by a person of ordinary skill in the art.

In step 836, longitudinal expansion of the coiled wire can be inhibited with the loop wire during delivery of the implant. The loop wire can be stretch resistant and be positioned such that the loop wire does not significantly elongate during delivery of the implant.

In step 840, the implant can be released by retracting the pull wire. When a physician retracts the pull wire, the distal end of the pull wire can move proximally to exit the loop opening. Once the loop wire is no longer held in place by the pull wire, the loop wire can retract from the locking portion on the implant, thereby releasing the implant.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

The descriptions contained herein are examples of embodiments of the invention and are not intended in any way to limit the scope of the invention. As described herein, the invention contemplates many variations and modifications of the delivery member, including alternative implant types, alternative geometries of component parts, alternative placement of component parts, alternative attachment means, alternative materials, alternative treatment applications, alternative methods for constructing component parts, etc. These modifications would be apparent to those having ordinary skill in the art to which this invention relates and are intended to be within the scope of the claims which follow.

What is claimed is:

1. A delivery member for delivering an implantable medical device to a target location of a body vessel, the delivery member comprising:
    a proximal hypotube;
    a flexible coil extending from a distal end of the proximal hypotube;
    a compressible distal hypotube extending from a distal end of the flexible coil;
    a lumen extending from a proximal end of the proximal hypotube, through the proximal hypotube, through the flexible coil, through the compressible distal hypotube, and to a distal end of the compressible distal hypotube;
    a sleeve extending along a majority of the flexible coil, wherein the sleeve is effective to inhibit radial expansion of the flexible coil;
    a stretch-resistant loop wire comprising a first end and a second end, each affixed to the proximal hypotube, the stretch-resistant loop wire further comprising a loop opening positioned approximate a distal end of the compressible distal hypotube,
    wherein the stretch-resistant loop wire is effective to inhibit longitudinal elongation of the flexible coil; and
    a pull wire extending through the lumen,
    wherein the stretch-resistant loop wire and the pull wire are positioned to secure the implantable medical device to the delivery member,
    wherein the stretch-resistant loop wire and the pull wire are movable to release the implantable medical device from the delivery member,
    wherein the stretch-resistant loop wire is under tension when the implantable medical device is secured to the delivery member,
    wherein the compressible distal hypotube is compressed due to tension in the stretch-resistant loop wire when the implantable medical device is secured to the compressible distal hypotube, and
    wherein the compressible distal hypotube is movable to decompress upon movement of the stretch-resistant loop wire and pull wire to release the implantable medical device.

2. The delivery member of claim 1, wherein the flexible coil is more flexible than one or both of the proximal hypotube and the compressible distal hypotube.

3. The delivery member of claim 1, wherein the flexible coil comprises:
    a non-radiopaque proximal coil extending from a proximal end of the flexible coil;
    a non-radiopaque distal coil extending from the distal end of the flexible coil; and
    a radiopaque central coil extending between the non-radiopaque proximal coil and the non-radiopaque distal coil.

4. The delivery member of claim 1, where in the flexible coil comprises:
    a wire wound to form the flexible coil and defining a portion of the lumen, the wire comprising a diameter measuring from about 0.0008 inch to about 0.005 inch.

5. The delivery member of claim 4, wherein the wire comprises a substantially circular cross section.

6. The delivery member of claim 1, further comprising:
    a distal portion length measurable from the distal end of the compressible distal hypotube to a proximal end of the flexible coil,
    wherein the distal portion length measures about 40 cm.

7. The delivery member of claim 1, wherein the compressible distal hypotube comprises a spiral cut.

* * * * *